United States Patent
Zrenner et al.

(10) Patent No.: US 10,507,335 B2
(45) Date of Patent: Dec. 17, 2019

(54) COIL ARRANGEMENT AND SYSTEM FOR TRANSCRANIAL MAGNETIC STIMULATION

(71) Applicant: Eberhard Karls Universitaet Tuebingen Medizinische Fakultaet, Tuebingen (DE)

(72) Inventors: Christoph Zrenner, Tuebingen (DE); Ulf Ziemann, Tuebingen (DE)

(73) Assignee: EBERHARD KARLS UNIVERSITAET TUEBINGEN MEDIZINIZCHE FAKULTAET GESCHWISTER-SCHOLL-PLATZ, Tuebingen (DE)

( * ) Notice: Subject to any disclaimer, the term of this patent is extended or adjusted under 35 U.S.C. 154(b) by 0 days.

(21) Appl. No.: 15/897,056

(22) Filed: Feb. 14, 2018

(65) Prior Publication Data
US 2018/0169429 A1    Jun. 21, 2018

Related U.S. Application Data

(63) Continuation of application No. PCT/EP2016/070499, filed on Aug. 31, 2016.

(30) Foreign Application Priority Data

Aug. 31, 2015   (DE) .......................... 10 2015 114 483

(51) Int. Cl.
*A61N 2/02* (2006.01)
*A61N 2/00* (2006.01)
*A61B 5/00* (2006.01)

(52) U.S. Cl.
CPC ............... *A61N 2/02* (2013.01); *A61N 2/006* (2013.01); *A61B 5/6814* (2013.01)

(58) Field of Classification Search
CPC ......... A61N 2/02; A61N 2/006; A61B 5/6814
See application file for complete search history.

(56) References Cited

U.S. PATENT DOCUMENTS

| | | | |
|---|---|---|---|
| 2002/0007128 A1 | 1/2002 | Ives et al. | |
| 2003/0074032 A1* | 4/2003 | Gliner ................. | A61B 5/0484 607/45 |

(Continued)

FOREIGN PATENT DOCUMENTS

| | | |
|---|---|---|
| DE | 10 2012 101 | 8/2013 |
| WO | WO-2008/070001 | 6/2008 |

(Continued)

OTHER PUBLICATIONS

Chen et al., "Real-time brain oscillation detection and phase-locked stimulation using auto-regressive spectral estimation and time-series forward prediction," IEEE transactions on biomedical engineering (2013) 60(3):753-762.

(Continued)

*Primary Examiner* — Kaylee R Wilson
(74) *Attorney, Agent, or Firm* — Rimon, P.C.

(57) ABSTRACT

The present disclosure relates to the field of medical technology and in particular to the field of transcranial magnetic stimulation. A coil assembly is presented comprising a housing; a magnetic coil, and an electrode arrangement; wherein the magnetic coil is arranged in the housing and is adapted for generating a magnetic field for transcranial magnetic stimulation, wherein the electrode arrangement is arranged on the housing and adapted for deriving an EEG signal, and wherein the magnetic coil and the electrode arrangement are arranged on top of each other. Further, an electrode arrangement and a system for transcranial magnetic stimulation are provided.

23 Claims, 4 Drawing Sheets

(56) References Cited

U.S. PATENT DOCUMENTS

| | | | |
|---|---|---|---|
| 2004/0059761 A1* | 3/2004 | Hively | A61B 5/4094 708/160 |
| 2004/0073104 A1* | 4/2004 | Brun del Re | A61B 5/0408 600/372 |
| 2010/0113959 A1 | 5/2010 | Leone et al. | |
| 2010/0210894 A1 | 8/2010 | Leone et al. | |
| 2010/0286747 A1* | 11/2010 | Sabesan | A61B 5/0476 607/45 |
| 2011/0015942 A1* | 1/2011 | Oakley | A61B 5/0006 705/2 |
| 2013/0338424 A1* | 12/2013 | Pascual-Leone | A61N 2/02 600/13 |

FOREIGN PATENT DOCUMENTS

| | | |
|---|---|---|
| WO | WO-2014/139029 | 9/2014 |
| WO | WO-2014/140432 | 9/2014 |

OTHER PUBLICATIONS

International Search Report for PCT/EP2016/070499, dated Nov. 10, 2016, 13 pages.
The International Bureau of WIPO, International Preliminary Report on Patentability and Written Opinion for International Application No. PCT/EP2016/070499, dated Mar. 6, 2018, 6 pages.

* cited by examiner

COIL ARRANGEMENT AND SYSTEM FOR TRANSCRANIAL MAGNETIC STIMULATION

CROSS REFERENCES TO RELATED APPLICATIONS

This application is a continuation of international patent application PCT/EP2016/070499, filed on bAug. 31, 2016 designating the U.S., which international patent application has been published in German language and claims priority from German patent application DE 10 2015 114 483.2, filed on Aug. 31, 2015. The entire contents of these priority applications are incorporated herein by reference.

BACKGROUND OF THE INVENTION

The present invention relates to the field of medical technology and in particular to the field of transcranial magnetic stimulation (TMS). The present invention relates to a coil assembly for transcranial magnetic stimulation, an electrode assembly and a system for transcranial magnetic stimulation.

Transcranial Magnetic stimulation (TMS) is a technique for non-invasively stimulating the human brain. In particular TMS can effect a depolarization or hyperpolarization of neurons in the brain. TMS hereby uses electromagnetic induction for inducing weak electrical currents in the brain by a rapidly changing time variant magnetic field. This enables, for example, activation of specific or general brain regions with minimal impairment of the patient or test person. TMS uses electromagnetic induction to transmit electrical energy through the scalp and skull without causing pain like direct percutaneous electrical stimulation through the skin.

For TMS, a conductive coil or magnetic coil (solenoid coil) is placed on the head or in the immediate vicinity of the head and a strong rapidly changing current is passed through the coil. This causes a magnetic field which penetrates the skull and tissue essentially unattenuated and painlessly. In order to induce a sufficiently strong current flow to depolarize neurons in the brain, the current in the coil usually starts and stops within a few hundred microseconds, or the current in the coil reverses its direction of flow within few hundred microseconds.

TMS is currently used in different forms. In so-called single-pulse TMS, a single pulse is provided to the coil. The so-called repetitive TMS (rTMS) provides a pulse train with several magnetic pulses over a defined period of time. Currently, numerous stimulation protocols with different stimulation patterns are in use. For example, in intermittent Theta Burst Stimulation (iTBS) 3 pulses with 10 milliseconds separation are triggered, and this triple pulse is repeated 5 times per second, wherein after several minutes of stimulation short pauses are provided, respectively. The protocols in use have a defined stimulation sequence that is pre-programed/predefined.

TMS can be used, for example, in medical research and for therapeutic applications in rehabilitation after stroke, neuropathic pain, tinnitus, depression or schizophrenia.

A conventional system for transcranial magnetic stimulation comprises a coil assembly and a stimulus generator that feeds the coil assembly. The coil assembly is sometimes referred to as "coil", the stimulus generator as "magnetic stimulation unit/device", "stimulator" or "magnetic stimulator unit".

Such TMS systems are already commercially available. Coil assemblies include, for example, ring-shaped coils or figure-of-eight-shaped coils by The Magstim Company Ltd, UK (e.g. "double 70 mm remote control coil") or by MagVenture, USA ("MagPro" coils). Examples of stimulus generators include the model Magstim Rapid by The Magstim Company Ltd, UK and the MagPro stimulators by MagVenture, USA. The coil assemblies can have a switch for manual triggering of a magnetic pulse by the stimulus generator. A stimulus generator can also have a trigger input for externally triggering a TMS pulse.

US 2002/0007128 A1 teaches that for reasons of patient safety and to monitor the efficacy of transcranial magnetic stimulation, it may be desirable to monitor a patient's electroencephalogram (EEG) during a TMS session. In addition to the TMS system, an EEG system is provided for the EEG measurement. The EEG electrodes are attached to the patient's scalp in a conventional way and connected to an EEG control unit. For the positioning of the electrodes on the scalp, US 2002/0007128 A1 refers to the arrangement according to the international 10-20 system.

WO 2014/139029 A1 discloses a positioning aid in the form of a positioning cap comprising alignment devices for alignment which interact with corresponding receptacles of a TMS coil assembly in order to fix the coil assembly in a desired position on the head of the test person with respect to the positioning aid. The positioning aid can have EEG electrodes. In a first step, the positioning aid/cap (without TMS coil assembly) is aligned and fixed to the skull of the test person. In a second step, the separate TMS coil assembly is aligned with and fixed to the positioning aid. A displacement of the TMS coil assembly with respect to the skull is thus prevented.

US 2002/0007128 A1 further discloses that a control system can be provided between the EEG system and the TMS system which can switch off the TMS system if necessary. A problem with TMS is that, in particular in case of strong stimulation of the patient's brain, cramping activity or a seizure may be caused by TMS. It is thus proposed to monitor the EEG of the patient and, if a cramping activity is recognized, to switch off the transcranial magnetic stimulation. It is further suggested to end the TMS if the brain of the patient is in a desired target state based on an evaluation of the EEG data.

US 2010/0210894 A1 discloses according to a first aspect, a hood-like device comprising a TMS coil arrangement and electrodes arranged in the vicinity of the coil arrangement. In an emergency situation this hood shall be placed over a patient's head quickly for terminating a seizure. According to a second aspect a helmet-like positioning aid is proposed. The positioning aid can have EEG electrodes. Similar to WO 2014/139029 A1 the positioning aid has fixation means on which a TMS coil assembly can be fixed at a defined location by corresponding fixation means. A helmet-like positioning aid to keep a TMS coil assembly in a predetermined position with respect to the user's head is also known from US 2010/0113959 A1.

US 2002/0007128 A1 further discloses that eddy currents may be induced in the metallic EEG electrodes by the TMS pulses. This can cause the electrodes to heat up. It is therefore suggested to use TMS-compatible plastic electrodes with an otherwise unchanged electrode arrangement.

WO 2014/140432 A1 also discloses monitoring of a patient's EEG during TMS for reasons of patient safety and to monitor efficacy. Since the TMS pulses can influence the EEG system, it is suggested to measure EEG data when there is no TMS pulse, e.g. immediately after a TMS pulse.

In Zrenner et al. "Brain-state dependent brain stimulation: Real-time EEG alpha band analysis using sliding window FFT phase progression extrapolation to trigger an alpha phase locked TMS pulse with 1 millisecond accuracy", First International Brain Stimulation Conference, 2-4 Mar. 2015, a previous publication by the inventors, it is described that a real-time electroencephalogram can be used for brain state dependent brain stimulation. This is also referred to as "EEG-TMS". To determine the brain state, a conventional EEG is measured in real time and the activity of the alpha waves is determined. For the positioning of the EEG electrodes on the scalp, an EEG cap is used so that the electrodes are arranged at defined positions and comparable results can be achieved. The phase position of the alpha waves is determined by means of a moving FFT window. Based on the detected phase position, the transcranial magnetic stimulation is triggered synchronized in phase.

Disadvantages of the above-mentioned solutions are the high complexity of the systems and the relatively complicated handling, including the long period of time required for setup, so that their use in everyday clinical practice does not appear to be practical in many cases. A doctor could therefore be inclined to prefer drug treatment over the use of a TMS system.

SUMMARY OF THE INVENTION

In view of this background, is can be among others an object underlying the present invention is to further improve a device for transcranial magnetic stimulation in that preferably a more targeted and thus more effective stimulation becomes possible and that the handling is facilitated. In particular, this device should enable application of a stimulation sequence which is not pre-programed and static as in conventional protocols, but is dynamically controlled by a simultaneously present brain activity (measured by an EEG measurement) of the individual person.

According to a first aspect of the present disclosure, there is provided a coil assembly comprising
a housing,
a magnetic coil, and
an electrode arrangement,
wherein the magnetic coil is arranged in the housing and is adapted for generating a magnetic field for transcranial magnetic stimulation,
wherein the electrode arrangement is arranged on the housing and adapted for deriving an EEG signal,
wherein the magnetic coil and the electrode arrangement may further be arranged on top of each other.

In other words, a coil assembly can be provided comprising a housing and a magnetic coil arranged therein for generating a magnetic field for transcranial magnetic stimulation, wherein the coil assembly further comprises an electrode arrangement arranged on the housing for deriving an EEG signal, wherein the magnetic coil and the electrode arrangement are arranged stacked/on top of each other.

It is thus suggested to provide an electrode arrangement for acquisition of an EEG signal directly at a housing of the coil assembly for TMS. The electrode arrangement can thus already be integrated in the coil assembly. A major advantage of this solution is that measurement of the brain activity of the patient or test person can be carried out directly where the magnetic coil is placed. Hence, there is a fixed positional relationship between the TMS coil and the EEG electrodes. Based on the EEG signal, a more targeted stimulation can be effected at exactly that location where the brain activity is measured, irrespective of where the coil assembly is placed.

It should be noted that in conventional EEG signal acquisition, the positioning of the electrodes is usually very closely monitored in order to obtain meaningful, comparable measurement results for different patients. In conventional examination with EEG, electrodes are attached to specific areas of the skull surface in order to measure cortical electrical activity. The positioning scheme depends on the number of electrodes. Usually the international 10-20 system is used. There is therefore a fixed positional relationship between the head of the test person and the EEG electrodes. As a positioning aid, an EEG cap with the large number of EEG electrodes at defined positions can be used. Thanks to the standardized positioning, measurement results of different patients can be compared with each other, for example to identify characteristic EEG patterns for seizures.

The inventors thus propose a different approach, in contrast to the conventional type of EEG measurement that is used in the prior art, since the electrode arrangement is rigidly attached to the housing of the coil assembly. The inventors have recognized that an EEG-based transcranial magnetic stimulation (EEG-TMS) can be readily performed based on an EEG signal which is acquired at the position of the coil assembly. In particular, it is thus not necessary for EEG-TMS to always record an EEG of the entire head.

The proposed solution may further provide an advantage that in an EEG-based transcranial magnetic stimulation an EEG activity of exactly that region of the brain is considered which is directly below the coil assembly and preferably stimulated by the TMS. For this purpose the magnetic coil and the electrode arrangement are arranged directly on top of each other. In particular no—potentially erroneous—assignment of one or more EEG electrodes of an EEG cap to a position of the coil assembly is required. Thereby the complexity of the system is further reduced and the handling facilitated.

Another advantage of the proposed solution may be that the magnetic pulse for transcranial magnetic stimulation is not shielded by other EEG electrodes such as in case of an EEG cap. A further advantage my thus also be that no further EEG electrodes can be heated by eddy currents induced by TMS magnetic pulses. Preferably the electrode assembly according to the proposed solution is thermally coupled with the coil assembly so that heat from the EEG electrodes can be dissipated via the coil assembly. In contrast thereto the prior art (US 2002/0007128 A1) suggests the use of polymer electrodes.

Further advantages may include simplified handling and time savings during operation because it is not necessary to first attach the EEG electrodes on the patient's scalp prior to the actual TMS procedure. The correct positioning of the EEG electrodes is usually associated with a high time expenditure of for example 30 min. In addition costs may be reduced with the proposed solution compared to separate EEG and TMS systems. Preferably, a therapeutic application, for example a 20 minute protocol 3 times a day can be made possible.

A further advantage may be that the EEG measurement can take place at/below the position from which the subsequent transcranial magnetic stimulation by the magnetic coil emanates. A further advantage may be a compact design.

Optionally, the magnetic coil may define a center and the electrode arrangement may be aligned with said center. Hence, the electrode arrangement may be arranged centered with respect to the magnetic coil.

An advantage of this embodiment may be that the positioning and thus the handling of the electrode arrangement is facilitated. The position of the magnetic coil is preferably marked on the top side of the coil assembly. When the coil assembly with the electrode arrangement at a lower side of the coil assembly is placed on the head of the patient, the operator, e.g. physician, can orientate himself/herself with respect to the position of the magnetic coil. The electrode arrangement and the magnetic coil can therefore be aligned and centered in the axial direction of the magnetic coil. The electrode arrangement can in particular be arranged in such a way that the electrodes of the electrode arrangement surround a center of the magnetic coil. A center of the magnetic coil can, for a ring-shaped coil, refer to the center of the ring. A center of the magnetic coil can, for a figure-off-eight-shaped coil (figure8-coil) can refer to the center of the eight, i.e., to the intersection of the left and right coil areas, or alternatively to a center of the right or left coil area.

The coil arrangement may have exactly one magnetic coil for generating a magnetic field for transcranial magnetic stimulation.

The coil can be implemented as a ring-shaped coil or a figure-off-eight-shaped coil or coil with a figure-off-eight-shaped winding. The coil preferably has a diameter between 30 mm and 150 mm, preferably between 40 mm and 120 mm, preferably between 50 mm and 90 mm.

The housing may further comprise a handle or a holding assembly.

With the handle or an alternative holding device or assembly, an operator, e.g. a physician, can move the coil assembly including the electrode arrangement freely along the patient's head and thereby select the desired position for the TMS. Further, a holding assembly can be designed in such a way that the coil arrangement can be attached to a holder. This may be advantageous if the same location is to be stimulated over an extended period of time.

The electrode arrangement may comprise at least a one of a dry electrode and a wet electrode. The electrode arrangement may comprise an electrode made of a superabsorbent polymer.

For TMS compatible EEG measurements according to the prior art gel-electrodes are usually used. However, in case of the proposed electrode arrangement, preferably the afore-mentioned dry electrodes or electrodes with a superabsorbent polymer are used. Such an electrode with superabsorbent polymer is known from DE 10 2012 101 337 A1. These electrodes are also referred to as "wet marble electrodes". Dry electrodes are for example commercially available from the company Cognionics Inc., USA. An advantage of the afore-mentioned electrodes over gel-electrodes may be that the coil arrangement can more easily be moved over the patient's head.

The electrode arrangement may comprise at least one fixed (or rigid) electrode and at least one spring electrode.

An advantage of spring electrodes may be that they can flexibly adapt to the shape of the user's head. Hence, a better contact and thus a better EEG signal can be achieved. One or more electrodes of the electrode arrangement can be implemented as spring electrodes. Spring electrodes can also be referred to as "spring-loaded electrodes". However, spring electrodes usually have a higher overall height. Preferably at least one electrode of the electrode arrangement is therefore not a spring electrode but a fixed or rigid electrode. The inventors have recognized that for the present application a combination of at least one spring electrode and at least one fixed electrode can be particularly advantageous. Due to the fixed electrode a smaller distance between the users head and the magnetic coil can be achieved. A smaller distance can lead to a better transcranial magnetic stimulation by the magnetic field generated by the magnetic coil. However, the combination of a fixed electrode with spring electrodes can at the same time allow flexible adjustment to a shape of the users head. As a result, the effect of the magnetic field, the EEG signal quality and/or the handling of the coil assembly can be improved thanks to the flexible adjustment.

A further advantage may be that the electrode arrangement can be quickly and easily positioned on the users skull. This may be particularly advantageous, if the TMS coil assembly is positioned freely, for example in order to be able to stimulate different areas of the brain in a flexible way.

In a further refinement the electrode arrangement may comprise at least one fixed electrode and a plurality of spring electrodes, wherein the spring electrodes surround the at least one fixed electrode.

For example one, two or three fixed electrodes can be provided, that are surrounded by further spring electrodes. The spring electrodes in the surrounding can flexibly adapt to the shape of the head of the user.

In a further refinement of the coil assembly, the at least one fixed electrode may be arranged centered with respect to the magnetic coil.

In other words, the at least one fixed electrode can be located in a central area of the magnetic coil (underneath the magnetic coil on the housing). An advantage of this embodiment may in particular be that due to the fixed electrode a small distance between the magnetic coil and the head can be achieved in a central area. In particular in a figure-off-eight-shaped coil the field maximum is formed in a central area of the magnetic coil. Hence, an improved coupling and improved transcranial magnetic stimulation in the center can be achieved.

The coil assembly may further comprise an integrated evaluation processor adapted for evaluating of the EEG signal. Alternative the evaluation processor can also be arranged in another part of the EEG based TMS system. For example, the evaluation processor can be connected to the coil assembly via a cable. The evaluation processor can also be integrated in the electrode arrangement.

An advantage of this embodiment may in particular be that no or only minimal changes may be necessary to the other components of the TMS system, in particular the stimulus generator. Preferably, a conventional stimulus generator with a trigger input can be used without further modification. The evaluation processor can be adapted to generate a trigger signal based on an evaluation of the EEG signal which is transmitted to a trigger input of the stimulus generator.

A further advantage may be that the EEG signal can be processed directly within the coil assembly. It is therefore not necessary to transfer raw EEG signals to other units.

In a further refinement, the evaluation processor may further be adapted to effect an adaptation of a parameter of the transcranial magnetic stimulation based on the EEG signal. In other words, the magnetic coil may be adapted to generate the magnetic field with a defined parameter, and the evaluation processor may be further adapted to effect an adaptation of the parameter. The evaluation processor may also be referred to as evaluation device or evaluation unit.

An advantage of this embodiment may be that the die transcranial magnetic stimulation can thereby be directly to the individual brain state represented by the EEG signal. In particular as a parameter, a point in time or an intensity, power or pulse energy, a duration and/or frequency of magnetic stimuli of the TMS can be adjusted. For example, the phase position of an alpha wave of the brain can be determined and the TMS pulse can be triggered based on the phase position of the alpha wave in that the evaluation processor transmits a corresponding trigger signal to a stimulus generator. Preferably, the EEG signal is evaluated in a real time data processing system (e.g. a LabView or Simulink real time model on an FPGA platform).

The determination of the instantaneous (i.e. at a time of possible stimulation) phase position of the EEG signal in a certain frequency band is not trivial since the signal processed and filtered in real time is necessarily delayed compared to the original signal (typically by about 100 milliseconds, i.e., a complete alpha wave). In a refinement, the evaluation processor may be adapted to determine the instantaneous phase position by combining one or more approaches.

A first approach implemented by the inventors in the present prototype may be dynamic DFT (discrete Fourier transform) of an immediately preceding EEG signal. The evaluation processor may be configured to, determine a phase position of the EEG signal in a predetermined frequency band, wherein, in a first step, a first frequency of the EEG signal is determined by means of a first spectral analysis of a first moving window of the EEG signal, and in a second step a phase of the EEG signal is determined by means of a second spectral or Fourier analysis of a second moving window of the EEG signal, wherein the first window is preferably wider than the second window, and wherein the width of the second window for the second spectral analysis is selected such that it corresponds to an integer multiple of a wavelength corresponding to the first frequency of the EEG signal or alternatively a DFT equation with a non-integer multiplication parameter adapted to the wavelength corresponding to the first frequency of the EEG signal is determined.

An advantage of this embodiment may be that the instantaneous phase position of the EEG signal can be determined as accurately as possible. The influence of artefacts can be reduced. In other words, a two-stage approach is suggested. In the first step, there is a coarse determination of a desired first frequency of the EEG signal. For example, the first desired frequency can be an alpha wave. In EEG measurements a signal in the frequency range between 8 and 13 Hz is referred to as alpha waves. In the first step a first frequency in a desired frequency range can thus be determined, for example the frequency with the highest amplitude in this frequency range. In the second step the width of the second window for the Fourier analysis is selected based on the determined first frequency such that it corresponds to an integer multiple of the wave-length at the determined first frequency. Hence, a form of a cascaded evaluation is proposed.

A second approach implemented by the inventors in the present prototype may be an autoregressive real time forward model, which determines the delay of the signal caused by the filtering by a forward calculation of the expected signal based on the previous signal and analyzes the phase of the forward calculated signal. Such an approach has been proposed in Chen L L, Madhavan R, Rapoport B I, Anderson W S, Real-Time Brain Oscillation Detection and Phase-Locked Stimulation Using Autoregressive Spectral Estimation and Time-Series Forward Prediction, IEEE transactions on bio-medical engineering, 2013;60(3):753-762.

The coil assembly may comprise a protective circuit adapted for disabling (switching off) at least one component for measuring the EEG signal during a magnetic pulse.

An advantage of this embodiment may be that damage of components for measuring the EEG signal during a magnetic pulse can be avoided. Preferably, the components for measuring the EEG signal without being affected by a TMS pulse may more quickly be available again for a subsequent EEG measurement.

The coil assembly may be further adapted to carry out, after generating the magnetic field, a reset of at least one component for at least one of measuring of the EEG signal, processing the EEG signal, and controlling a parameter for transcranial magnetic stimulation.

A magnetic pulse or magnetic field generated by the magnetic coil for transcranial magnetic stimulation can impair functionality of components for measuring the EEG signal. Preferably after such a magnetic pulse, a reset or new start of at least one component for measuring the EEG signal and/or for processing the EEG signal and controlling a stimulation parameter for transcranial magnetic stimulation may be carried out. For example an analog-to-digital-converter for digitizing a raw EEG signal is reinitialized. An advantage of this as well as the previous embodiment may be that artifacts can be avoided and/or a control electronic can be made robust against interferences by the magnetic pulse.

The coil assembly may further comprise a reference electrode.

An advantage of this embodiment may be that by means of the reference electrode a reference potential for the EEG signal can be provided. The reference electrode can for example be adapted for attachment to a (substantially) electrically neutral location such as an earlobe or a collarbone. The reference electrode can be connected to the coil assembly via a cable.

Further, the coil assembly may comprise one or more additional fixed EEG electrodes connected via a cable (e.g. also gel-electrodes that are applied, or a net, or e.g. also electrodes that are included in a headband), e.g. for measuring the effect of the stimulation on evoked EEG potentials in brain regions that are spaced further apart from the stimulation electrode as effect parameters.

The coil assembly may comprise an electrode for deriving/measuring an EMG signal.

An advantage of this embodiment may be that the proposed assembly enables application of a transcranial stimulation sequence, that is controlled via EMG (electromyogram) measured muscle activity of the individual person. Preferably, the evaluation processor can be adapted to effect an adaptation of a parameter of the transcranial magnetic stimulation based on the EMG signal. Hence, a brain state dependent brain stimulation based on the EEG signal and/or the EMG signal can take place. The coil assembly can comprise one or more, also additional, in particular connected via a cable, further biosignal electrodes, e.g. EMG measurements for measuring the effect of the stimulation on evoked muscle potentials as effect parameters.

According to a second aspect of the present disclosure an electrode arrangement or assembly for acquisition or deriving an EEG signal is provided, wherein the electrode arrangement comprises a mount adapted to the housing of a coil assembly, wherein the coil assembly comprises a magnetic coil arranged in the housing and adapted for generating a magnetic field for transcranial magnetic stimulation, and wherein the electrode arrangement is adapted to be attached to the housing of the coil assembly by means of the mount, such that the magnetic coil and the electrode arrangement are arranged on top of each other.

The afore-mentioned solution may thus enable retrofitting a TMS coil assembly or a TMS system with EEG functionality as explained in detail in accordance with the first aspect of the present disclosure. In other words, an existing coil assembly can be retrofitted with EEG functionality. The proposed electrode arrangement/assembly with mount can thus be understood as a type of adapter or electrode extension for an existing TMS coil arrangement. In combination with a coil assembly, the proposed electrode adapter thus offers the same advantages as the coil assembly with electrode arrangement according to the first aspect of the present disclosure.

The electrode arrangement may comprise an integrated evaluation processor adapted for evaluating the EEG signal and optionally for generating a trigger signal. Generally, the electrode arrangement may comprise an evaluation processor. The evaluation processor can alternatively also be connected to the electrode arrangement via a cable. The evaluation processor may be adapted for modulating a parameter of an algorithm that generates a trigger signal.

An advantage of this embodiment may be that no or only minimal changes may be necessary to other components of a TMS system, in particular to the coil arrangement and the stimulus generator. Preferably, a conventional stimulus generator with trigger input may be used without further modifications. The evaluation processor can be adapted to generate a trigger signal based on an evaluation of the EEG signal, which trigger signal is transmitted to a trigger input of the stimulus generator.

According to a third aspect of the present disclosure a system for transcranial magnetic stimulation is provided. The system may comprise:
  a coil assembly;
  a stimulus generator; and
  a controller;
  wherein the coil assembly comprises a housing, a magnetic coil, and an electrode arrangement; wherein the magnetic coil is arranged in the housing and is adapted for generating a magnetic field for transcranial magnetic stimulation; wherein the electrode arrangement is arranged on the housing and adapted for deriving an EEG signal, wherein the magnetic coil and the electrode arrangement are arranged on top of each other;
  wherein the stimulus generator is adapted for generating a transcranial magnetic stimulus; and
  wherein the controller is adapted for controlling the stimulus generator based on the EEG signal.

A system for transcranial magnetic stimulation may thus comprise: a coil assembly according to the first aspect of the disclosure; or a coil assembly and an electrode arrangement according to the second aspect of the disclosure as described above; a stimulus generator adapted for generating a transcranial magnetic stimulus; and a controller adapted for controlling the stimulus generator.

In other words, the system can, on the one hand, comprises a coil assembly with an electrode arrangement that is already arranged on the housing or integrated therein. On the other hand, the system can comprise a conventional coil assembly and in addition an electrode arrangement for recording an EEG signal, that can be attached to the housing of the coil assembly with a mount. Preferably, the housing of the coil assembly may already comprise means for attaching the mount, as for example recesses in a housing of the coil assembly for engaging snap hooks of the mount of the electrode arrangement.

The stimulus generator connected with the coil assembly can, by passing current through the coil arrangement in a known way, generate a transcranial magnetic stimulus. In other words, a magnetic pulse can be generated by the magnetic coil by a current provided by the stimulus generator, which may cause transcranial magnetic stimulation. Such a magnetic pulse is thus referred to as a transcranial magnetic stimulus in the present disclosure.

It is to be understood that the afore-mentioned electrode arrangement/assembly and the afore-mentioned system according to the second and third aspect of the disclosure may have identical or similar embodiments and/or advantages as the coil assembly according to the first aspect of the disclosure. Elements that are provided in the coil assembly may alternatively also be provided in the electrode arrangement or in the system, for example in the control unit of the system. For example the evaluation processor can be arranged in the coil assembly, the electrode arrangement or the control unit.

Further advantages will be apparent from the description and the attached figures.

It is to be understood that the afore-mentioned and following features may not only be used in the given combination but also in other combinations or alone without leaving the scope of the present invention.

BRIEF DESCRIPTION OF THE DRAWINGS

Embodiments of the disclosure are provided in the attached figures and will be explained in more detail in the following description.

DESCRIPTION OF PREFERRED EMBODIMENTS

Figure 1:
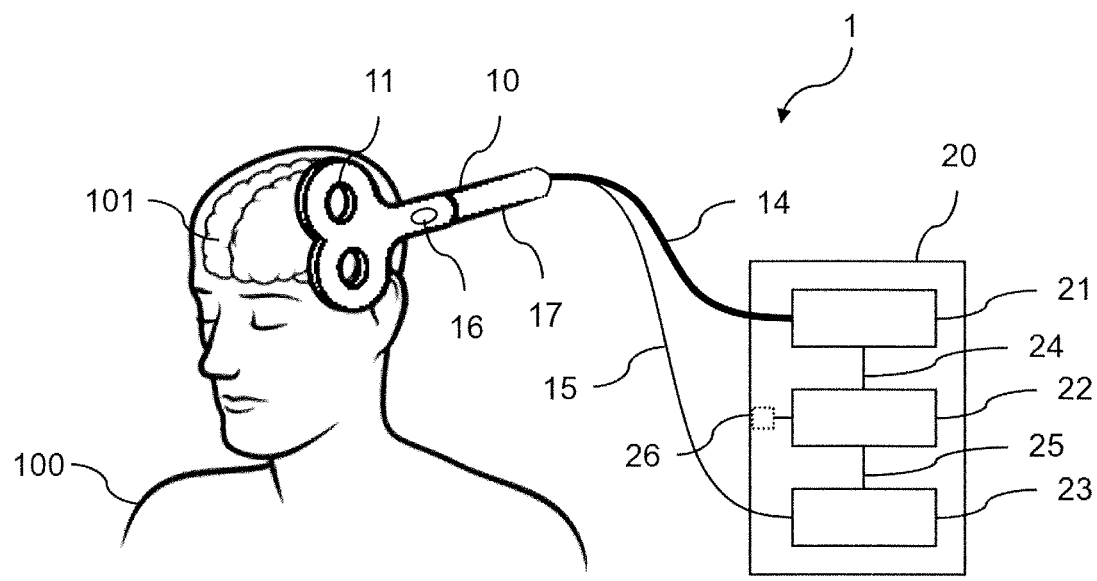
FIG. 1 shows a schematic diagram of a system for transcranial magnetic stimulation (TMS) according to an embodiment of the disclosure.

FIG. 1 shows a schematic diagram of a system for transcranial magnetic stimulation (TMS) of the brain 101 of a patient 100 according to an embodiment of the disclosure. The system is denoted in its entirety by reference numeral 1.

Figure 2:
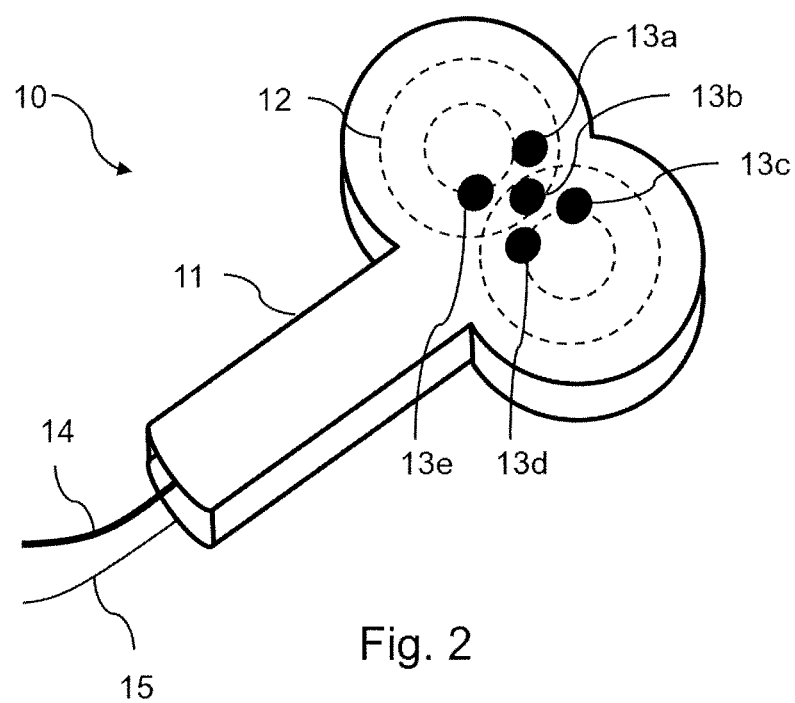
FIG. 2 shows a bottom view of a coil assembly for transcranial magnetic stimulation with an integrated electrode arrangement according to an embodiment of the disclosure.

FIG. 2 shows a bottom view of a coil assembly 10 for a transcranial magnetic stimulation of FIG. 1. On its lower side, the coil assembly 10 comprises an integrated electrode arrangement 13, which is exemplarily shown by the electrodes 13a to 13e.

The system 1 for transcranial magnetic stimulation in this embodiment comprises a coil assembly 10 and a stimulation unit 20. The stimulation unit 20 comprises a stimulus generator 21 for generating a transcranial magnetic stimulus, a control unit 22 for controlling the stimulus generator 21 and an evaluation processor 23. The evaluation processor 23 may also be arranged for example in the coil assembly 10.

The coil assembly 10 comprises a housing 11 and a magnetic coil 12 arranged therein for generating a magnetic field for transcranial magnetic stimulation, wherein the coil assembly 10 further comprises an electrode arrangement 13 arranged at the housing 11 for acquisition of an EEG signal. The magnetic coil 12 in the housing 11 is shown in FIG. 2 by a dashed figure-off-eight coil configuration. Alternatively other coil configurations or another coil geometry such as a ring-coil can be used.

In order to perform the TMS on the brain 101 of a patient 100, the coil assembly 10 can first be brought into contact with the patient's 100 scalp with the electrodes 13a-13e. The housing 11 of the coil assembly can have a handle 17 for this purpose with which the coil assembly 10 can be held by an operator such as a physician. By means of the electrodes 13a-13e an EEG signal of the patient 100 can be acquired. The EEG signal or a plurality of EEG signals can be transmitted to an evaluation processor 23 via a signal line 15. Alternatively, the signal transmission can also be wireless.

The evaluation processor 23 evaluates the EEG signal and generates, based on the EEG signal, a trigger signal 25 that is transmitted to the control unit 22. Preferably, the evaluation processor can determine a phase position of for example the alpha waves of the EEG signal in real time and generate a corresponding trigger signal. An advantageous embodiment of an evaluation processor is explained further below with reference to FIGS. 5 and 6.

The control unit 22 generates in response to the trigger signal 25 a control signal 24 for controlling the stimulus generator 21. The stimulus generator 21 generates a strong rapidly changing current in response to the control signal 24, which is passed over the power line 14 to the magnetic coil 12 in the coil assembly 10. As described above, this generates a magnetic field or magnetic pulse, which induces a current in the brain 101 of the patient 100.

By this stimulation, a state of the brain 101 of the patient 100 can favorably be influenced. The brain state after such a stimulus can again be evaluated with the EEG electrodes 13 and the evaluation processor 23 and a new stimulus can be triggered. This preferably results in a closed loop control for EEG-based transcranial magnetic stimulation (EEG-TMS).

Since the electrodes 13a-13e are directly arranged at the housing 11 of the coil arrangement 10, the stimulation is always carried out at the exact location where the underlying EEG signal was measured. A targeted TMS can thus be carried out in a simple manner.

Optionally, the coil assembly can further comprise a trigger switch 16 for manually triggering a magnetic pulse or a TMS sequence. The power line 14 and the signal line 15 are exemplarily shown as separate lines, but may also be included in one cable, which simplifies the handling. Optionally, the evaluation unit 23 comprises a protective circuit adapted for disabling at least one component for measuring the EEG signal during a magnetic pulse.

The electrodes 13a-13e are exemplarily implemented as dry electrodes, such that the coil assembly 10 can be moved on the head of the patient 100 so that an EEG measurement and corresponding stimulation of different regions of the brain can be carried out.

As shown in FIG. 2, the magnetic coil 12 and the electrode arrangement 13 are arranged on top of each other. In particular the electrodes 13a,13c,13d,13e are, in an exemplary configuration, arranged around a center of the magnetic coil 12. The EEG measurement can thus occur centered where the magnetic coil 12 stimulates. The electrode arrangement 13 further comprises a central electrode 13b. In other words, the EEG measurement can thus be carried out with an electrode arrangement in a fixed positional relationship to the magnetic coil 12, which electrode arrangement is located directly underneath the magnetic coil 12. Due to the central arrangement an EEG measurement can, in particular when using a figure-off-eight-shaped magnetic coil 12, be carried out near the field maximum. It is to be understood that the electrode arrangement can also comprise a plurality of centrally arranged electrodes or electrodes arranged around a center of the magnetic coil 12.

The control unit 22 can preferably comprise an external trigger input 26. For example if the evaluation processor 23 is arranged in the coil assembly 10 instead of the stimulation unit 20, the evaluation processor can then, via the control line 15, which can then be connected to the trigger input 26, a trigger signal to the control unit 22 of the stimulation unit 20 and thus trigger a magnetic stimulus.

Figure 3:
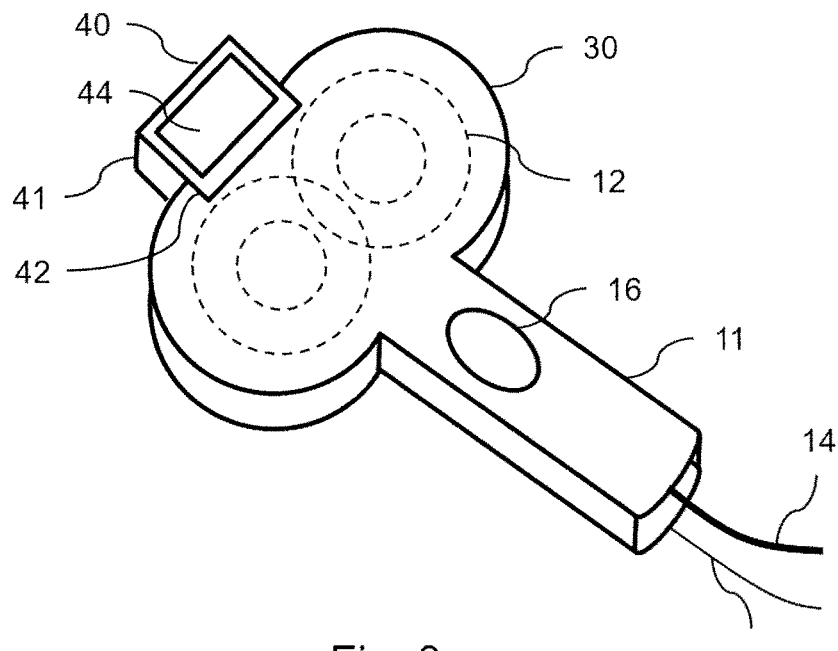
FIG. 3 shows a top view of a coil assembly with an electrode assembly in form of an adapter according to an embodiment of the disclosure.
Figure 4:
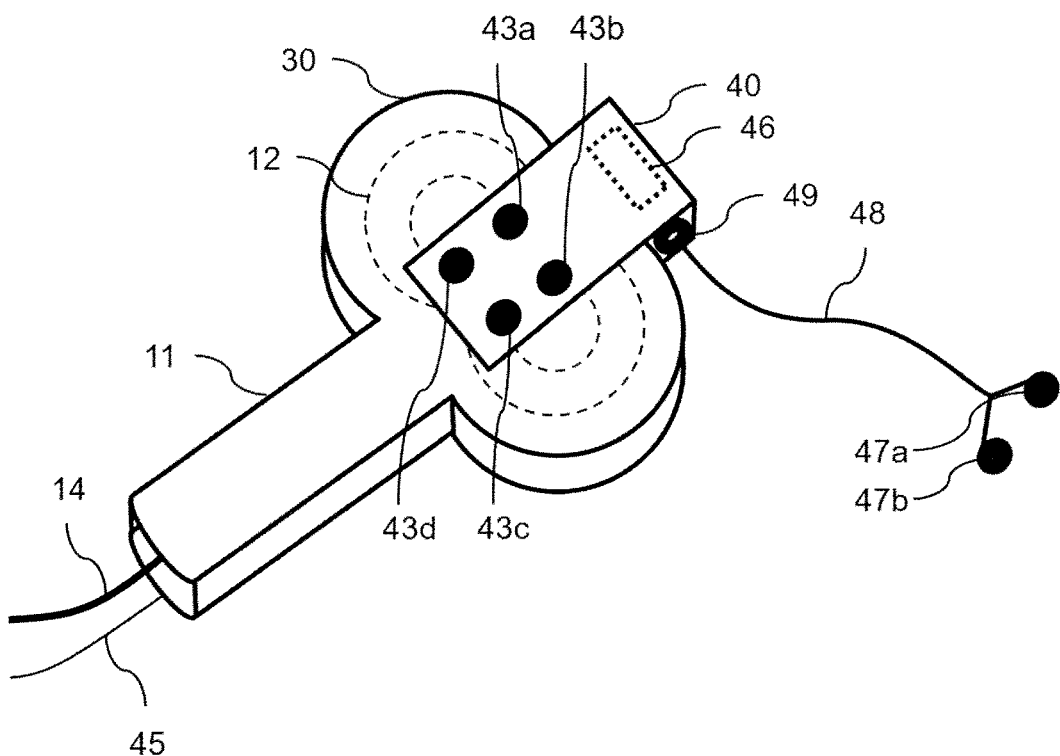
FIG. 4 shows a bottom view of the coil assembly with the electrode assembly in form of an adapter according to FIG. 3.

FIG. 3 shows a top view of a coil assembly 30 with an electrode arrangement or assembly 40 in form of an adapter according to an embodiment of the disclosure. FIG. 4 shows a bottom view of the coil assembly 30 with the electrode arrangement 40 in form of an adapter according to FIG. 3.

The electrode arrangement or assembly 40 for acquisition of an EEG signal comprises a holder or mount 41, that is adapted to the housing 11 of the coil assembly 30, wherein the coil assembly 30 comprises a magnetic coil 12 arranged in the housing 11 for generating a magnetic field for transcranial magnetic stimulation, and wherein the electrode arrangement 40 is attached to the housing 11 of the coil assembly 10 by means of the mount 41.

As an alternative to the example shown in FIG. 1 and FIG. 2, in which the electrode arrangement 13 forms part of the coil assembly 10, the electrode arrangement 40 according to FIG. 3 and FIG. 4 can thus also be retrospectively attached to an already existing coil assembly 30. Such coil assemblies 30 without EEG electrodes are known from the prior art and commercially available.

The mount 41 can for example comprise a U-shaped profile which can be attached to or slid onto a front side of the coil assembly 30. An upper side of the mount 41 can thus reach over or embrace an upper side of the coil assembly 42. A lower side of the mount 41 comprises a plurality of EEG electrodes 43a-43d and reaches over a lower side of the coil assembly 30. The coil assembly 30 can thus be inserted into or embraced by the mount 41 of the electrode arrangement 40, preferably clamped therein. The electrode arrangement 40 is thus attached to the coil assembly 30.

The electrode arrangement 40 can optionally comprise a user interface (HMI, Human-Machine-Interface). An advantage of this embodiment is that the operator can be given immediate feedback regarding the measured EEG signal. Based on this feedback the operator may, for example, check the positioning of the coil assembly 30 and the electrode arrangement 40 and adjust them if necessary.

Preferably the electrode arrangement 40 comprises an integrated evaluation processor 26, as indicated in FIG. 4.

The evaluation processor can evaluate EEG signals acquired by the EEG electrodes 43a-43d and generate a trigger signal based on the evaluation.

As shown in FIG. 3 and FIG. 4 the coil assembly 30 further comprises a power line 14, which can be connected to a stimulus generator 21 of a stimulation unit 20 according to FIG. 1. The electrode arrangement 40 comprises a control line 45, which can be connected to a trigger input 26 of the control unit 24 of a stimulation unit according to FIG. 1.

Optionally, the electrode arrangement 40 further comprises at least one reference electrode 47a, 47b that can be positioned on a substantially electrically neutral location on the body of the test person and serve as reference for the EEG measurement. The reference electrode 47a or 47b can be connected to an input 49 of the electrode arrangement 40 by means of a cable 48.

Optionally the electrode arrangement 40 comprises at least one EMG electrode, i.e., an electrode for acquisition of an electromyogram. It can be implemented as an EMG electrode 47a, 47b, as shown in FIG. 4. The EMG electrode can be connected with a cable 48 to an input 49 of the electrode arrangement. It is to be understood that both an EMG electrode as well as a reference electrode can be provided. Preferably an EEG signal acquired by means of an EEG electrode and an EMG signal acquired by means of an EMG electrode are provided to the evaluation processor (46). They can be considered by the evaluation processor in determining a parameter for transcranial brain stimulation. It is to be understood that an EMG electrode may also be arranged on other elements of the TMS system as shown in FIG. 1. For example an EMG signal can directly be provided to an evaluation processor 23 in a stimulation unit 20.

Figure 5:
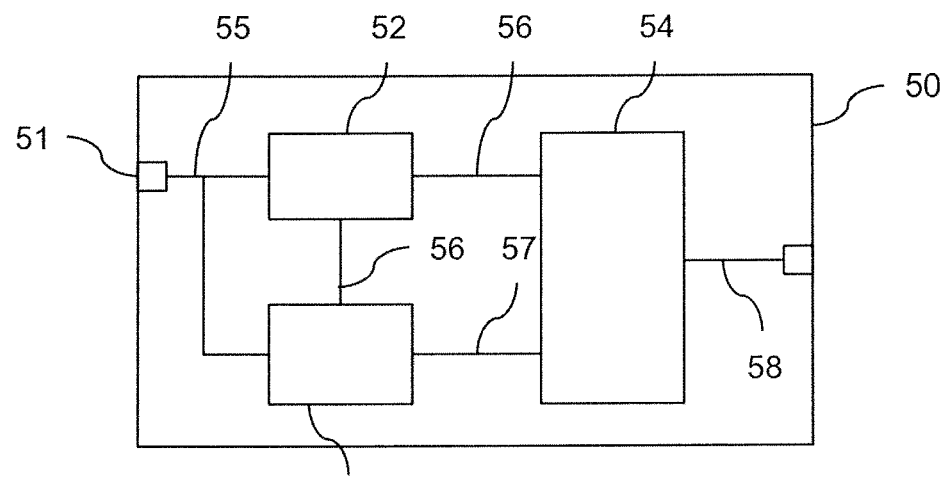
FIG. 5 shows a schematic diagram of an evaluation processor according to an embodiment of the disclosure.

FIG. 5 shows a schematic diagram of an advantageous embodiment of an evaluation processor or unit 50 according to an embodiment of the disclosure. For example this can be an evaluation processor unit 23 according to FIG. 1 or evaluation processor or unit 46 according to FIG. 4.

The evaluation processor 50 comprises an input 51 for receiving an EEG signal 55. The input 51 can for example comprise an amplifier and an analog-to-digital-converter (ADC). The EEG signal 55 is provided to a first DFT (Discrete Fourier Transform) or in particular FFT (Fast Fourier Transform) unit 52 and a second DFT or FFT unit 53. The first FFT unit 52 is adapted to perform a Fourier analysis or Fourier transform of the EEG signal. A sliding or moving window of the EEG signal is considered which has a fixed window width. In a desired frequency range, for example from 8-13 Hz for alpha waves or from 13-30 Hz for beta waves a first frequency 56 is determined. This can for example be the peak frequency in the desired frequency range.

Based on this first frequency 56 determined by the first FFT unit 52, a width of the window of the second FFT unit 53 is selected such that it corresponds to an integer multiple of the wavelength corresponding to the first frequency 56. Further, a width of the second FFT window is chosen smaller than the width of the first FFT window. Compared to the result of the Fourier analysis with the first FFT unit 52, artifacts can be reduced or avoided and a more precise phase determination of the EEG signal at the desired frequency can be achieved.

The phase 57 determined thereby is provided to a trigger signal generation unit 54 which generates a trigger signal 58 and makes it available at an output. The output can in turn be connected to an external trigger input 26 of a stimulation unit 20 as shown in FIG. 1.

Figure 6:
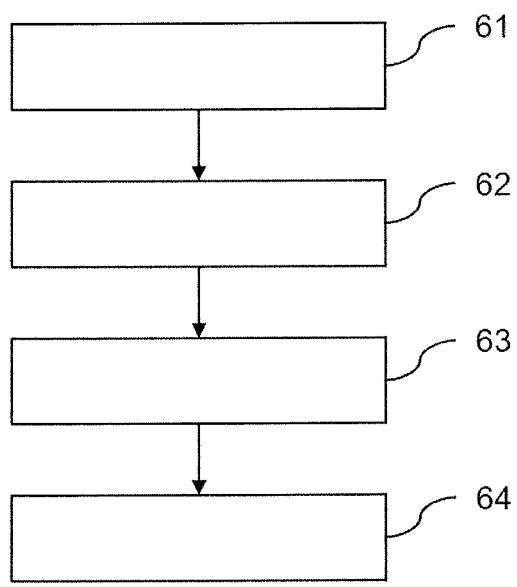
FIG. 6 shows a flow chart for evaluating an EEG signal according to an embodiment of the disclosure.

FIG. 6 shows a corresponding flow chart for evaluating an EEG signal 55 according to an embodiment of the disclosure.

In step 61 an EEG signal is received.

In step 62 a first frequency of the EEG signal is determined by means of a first Fourier analysis of the EEG signal in a first moving window. The first frequency can for example be a frequency with maximum amplitude in a desired frequency band, for example alpha waves as an indicator of a brain state.

In step 63 a phase of the EEG signal is determined by means of a second Fourier analysis of the EEG signal in a second moving window. Therein, the second window is smaller than the first window. Hence, a shorter section of the EEG signal is considered, in particular since it is to be assumed that this is subject to smaller variations. The width of the second window for the second Fourier analysis is selected such that it corresponds to an integer multiple of a wavelength corresponding to the first frequency of the EEG signal as determined in step 62.

In step 64 a trigger signal is generated based on the determined phase of the EEG signal, which triggers a magnetic pulse for transcranial magnetic stimulation.

Figure 7:
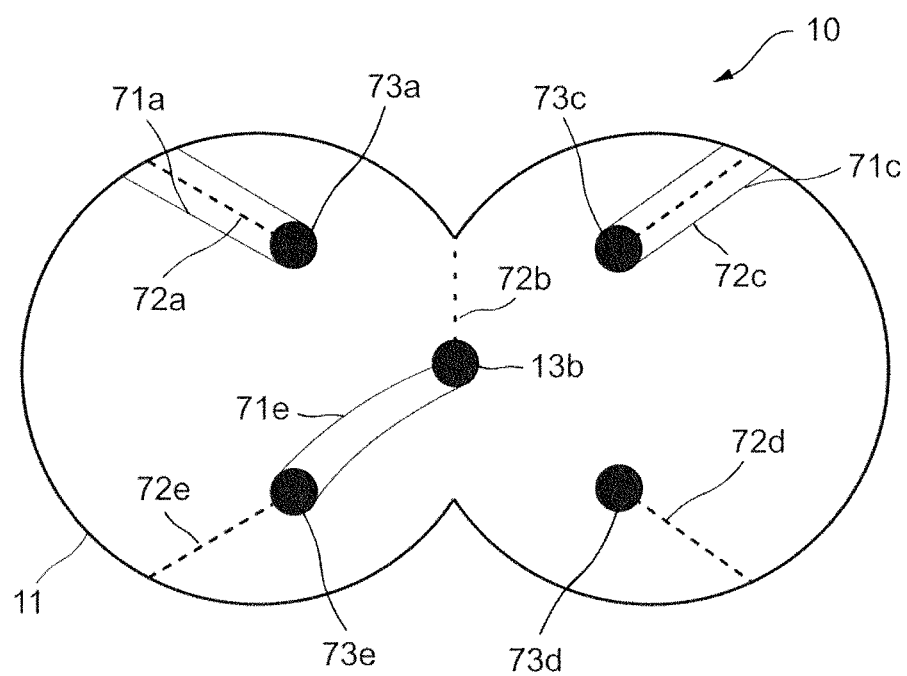
FIG. 7 shows a bottom view of a coil assembly for transcranial magnetic stimulation comprising an integrated electrode arrangement with at least one fixed electrode and a plurality of spring electrodes according to an embodiment of the disclosure.
Figure 8:
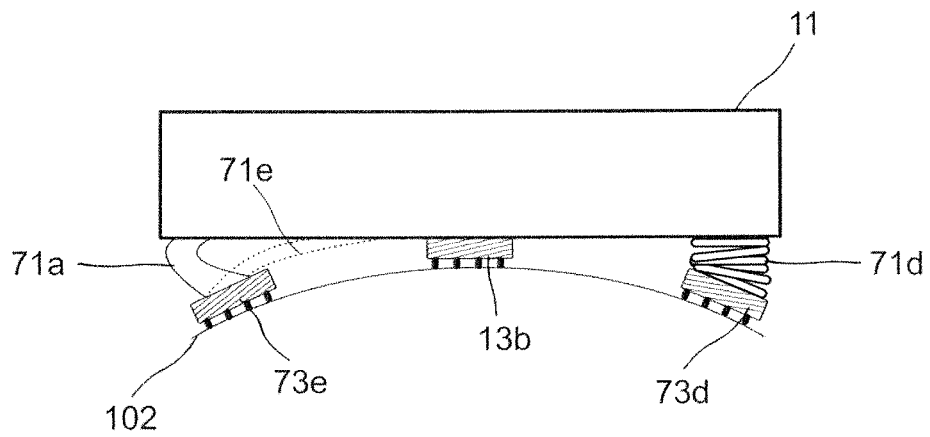
FIG. 8 shows a side view of the coil assembly according to FIG. 7.

FIG. 7 and FIG. 8 show a bottom view and a side view of an advantageous embodiment of a coil assembly for transcranial magnetic stimulation with an integrated electrode arrangement with at least one fixed electrode and a plurality of spring electrodes. It is to be understood that such an electrode arrangement comprising a combination of at least one fixed electrode and at least one spring electrode can advantageously also be used in an electrode assembly with a mount, as exemplarily shown in FIG. 4.

In the embodiment shown in FIG. 7, the electrode arrangement 13, for example, comprises four spring electrodes 73a, 73c, 73d, 73e, which surround a fixed electrode 13b. However, several fixed electrodes and/or a different number of spring electrodes can be provided. Advantageously, the fixed electrode 13b or the multiple fixed electrodes are arranged in a central region or around a central region of the magnetic coil 12. Thereby, a distance between the magnetic coil 12 and the skull 102 of the user can be minimized there.

As shown in FIG. 8, a fixed electrode 13b may enable a very short distance between the magnetic coil arranged in the housing 11 and the skull 102 of the user. On the other hand, spring electrodes 73a, 73c, 73d, 73e typically have a higher height. A spring characteristic of the spring electrodes can be achieved in various ways, for example by means of a spiral spring 71d, a leaf spring 71e or an elastic material 71a, as shown in FIG. 8.

An advantage of the spring electrodes is that they can flexibly adapt to a form of the skull 102 of the user 100, as exemplarily shown in the side view of FIG. 8 for spring electrodes 71a, 71d and 71e. Thereby, the proposed electrode arrangement 10 can quickly and easily be positioned at different positions of the head of the user 100. The proposed combination of fixed electrode 13b and spring electrodes 71a, 71c, 71d and 71e thereby combines the advantages of a targeted, effective transcranial magnetic stimulation of different brain areas with improved handling.

In an embodiment, a spring element can advantageously be arranged such that it faces away from a central region of the coil assembly 10. Thereby, a reduced impairment of the strong magnetic field in the central region can be achieved. As shown in FIG. 7, the spring element 71e for example a leaf spring, pointing into the central area, whereas the spring elements 71a and 71c face way from the coil assembly 10.

The electrodes further comprise signal lines 72a to 72e. They are preferably also arranged in such a way that a central area of the coil assembly 10 is avoided. In particular a voltage induced by the magnetic pulse on the signal lines can be reduced thereby.

With the proposed solution, a phase synchronous EEG-based transcranial magnetic stimulation may thus be performed with high precision, for example in rehabilitation after stroke or in the treatment of neuropathic pain, tinnitus or depression.

What is claimed is:

1. A coil assembly comprising a housing,
a magnetic coil, and
an electrode arrangement,
wherein the magnetic coil is arranged in the housing and is adapted for generating a magnetic field for transcranial magnetic stimulation,
wherein the electrode arrangement is arranged on the housing and adapted for deriving an electroencephalogram (EEG) signal, and
wherein the electrode arrangement is entirely confined within the perimeter of the magnetic coil.

2. The coil assembly of claim 1, wherein the magnetic coil defines a center and wherein the electrode arrangement is aligned with said center.

3. The coil assembly according to claim 1, wherein the magnetic coil comprises exactly one magnetic coil for generating the magnetic field for the transcranial magnetic stimulation.

4. The coil assembly according to claim 1, wherein the housing further comprises a handle.

5. The coil assembly according to claim 1, wherein the electrode arrangement comprises at least one of a dry electrode and a wet electrode.

6. The coil assembly according to claim 1, wherein the electrode arrangement comprises an electrode made of a superabsorbent polymer.

7. The coil assembly according to claim 1, wherein the electrode arrangement comprises at least one fixed electrode and at least one spring electrode.

8. The coil assembly according to claim 7, wherein the at least one spring electrode comprises a plurality of spring electrodes that surround the at least one fixed electrode.

9. The coil assembly according to claim 7, wherein the at least one fixed electrode is arranged centered with respect to the magnetic coil.

10. The coil assembly according to claim 1, further comprising an integrated evaluation processor adapted for evaluating the EEG signal.

11. The coil assembly according to claim 10, wherein the evaluation processor is further adapted to effect an adaptation of a parameter of the transcranial magnetic stimulation based on the EEG signal.

12. The coil assembly according to claim 10, wherein the evaluation processor is further configured to determine a phase position of the EEG signal in a predetermined frequency band, wherein
in a first step, a first frequency of the EEG signal is determined by a first spectral analysis of a first moving window of the EEG signal, and,
in a second step, a phase of the EEG signal is determined by a second spectral analysis of a second moving window of the EEG signal, and
wherein the width of the second window for the second spectral analysis is selected such that the width of the second window corresponds to an integer multiple of a wavelength corresponding to the first frequency of the EEG signal; or alternatively a discrete Fourier transform (DFT) equation with a non-integer multiplication parameter adapted to the wavelength corresponding to the first frequency of the EEG signal is determined.

13. The coil assembly according to claim 12, wherein the first window is wider than the second window.

14. The coil assembly according to claim 1, wherein the coil assembly comprises a protective circuit adapted for disabling at least one component for measuring the EEG signal during a magnetic pulse.

15. The coil assembly according to claim 1, wherein the coil assembly is further adapted to carry out, after generating the magnetic field, a reset of at least one component for at least one of measuring of the EEG signal, processing of the EEG signal, and controlling a parameter for the transcranial magnetic stimulation.

16. The coil assembly according to claim 1, wherein the coil assembly comprises a reference electrode.

17. The coil assembly according to claim 1, wherein the coil assembly comprises an electrode for deriving an electromyogram (EMG) signal.

18. The coil assembly according to claim 1, wherein the electrode arrangement is arranged underneath the magnetic coil.

19. The coil assembly according to claim 18, wherein the coil assembly is further adapted to carry out, after generating the magnetic field, a reset of at least one component for at least one of measuring of the EEG signal, processing of the EEG signal, and controlling a parameter for the transcranial magnetic stimulation.

20. The coil assembly according to claim 1, wherein the electrode arrangement comprises at least one fixed electrode and at least one spring electrode, wherein
the at least one spring electrode comprises a plurality of spring electrodes that surround the at least one fixed electrode, and
the at least one fixed electrode is arranged centered with respect to the magnetic coil.

21. An electrode arrangement adapted for deriving an EEG signal, wherein the electrode arrangement comprises a mount, adapted for attachment to a housing of a coil assembly, wherein the coil assembly comprises a magnetic coil arranged in the housing and adapted for generating a magnetic field for transcranial magnetic stimulation, and wherein the electrode arrangement is adapted to be attached to the housing of the coil assembly by the mount, such that the electrode arrangement is entirely confirmed within the perimeter of the magnetic coil.

22. The electrode arrangement according to claim 21, wherein the electrode arrangement comprises an integrated evaluation processor adapted for evaluating the EEG signal and further adapted for generating a trigger signal.

23. A system for transcranial magnetic stimulation comprising:
a coil assembly;
a stimulus generator; and
a controller;
wherein the coil assembly comprises:
a housing,
a magnetic coil, and
an electrode arrangement,
wherein the magnetic coil is arranged in the housing and is adapted for generating a magnetic field for transcranial magnetic stimulation, wherein the electrode arrangement is arranged on the housing and adapted for deriving an EEG signal,
wherein the electrode arrangement is entirely confined within the perimeter of the magnetic coil;
wherein the stimulus generator is adapted for generating a transcranial magnetic stimulus; and wherein the controller is adapted for controlling the stimulus generator based on the EEG signal.

* * * * *